(12) United States Patent
Bruins et al.

(10) Patent No.: US 11,686,732 B2
(45) Date of Patent: Jun. 27, 2023

(54) METHOD AND SYSTEM FOR THE NON-DESTRUCTIVE IN OVO DETERMINATION OF FOWL GENDER

(71) Applicant: IN OVO HOLDING B.V., Leiden (NL)

(72) Inventors: Wouter Sebastiaan Bruins, Leiden (NL); Wil Marijn Stutterheim, Leiden (NL); Thomas Hankemeier, Leiden (NL)

(73) Assignee: IN OVO HOLDING B.V., Leiden (NL)

( * ) Notice: Subject to any disclaimer, the term of this patent is extended or adjusted under 35 U.S.C. 154(b) by 1163 days.

(21) Appl. No.: 16/302,812

(22) PCT Filed: May 24, 2017

(86) PCT No.: PCT/NL2017/050330
§ 371 (c)(1),
(2) Date: Nov. 19, 2018

(87) PCT Pub. No.: WO2017/204636
PCT Pub. Date: Nov. 30, 2017

(65) Prior Publication Data
US 2020/0116730 A1 Apr. 16, 2020

(30) Foreign Application Priority Data

May 24, 2016 (NL) .................................... 2016818
May 24, 2016 (NL) .................................... 2016819
Aug. 29, 2016 (NL) .................................... 2017382

(51) Int. Cl.
| | |
|---|---|
| *G01N 33/68* | (2006.01) |
| *G01N 30/72* | (2006.01) |
| *G01N 30/88* | (2006.01) |
| *G01N 33/08* | (2006.01) |
| *G01N 33/48* | (2006.01) |
| *A01K 43/00* | (2006.01) |
| *G01N 33/483* | (2006.01) |

(52) U.S. Cl.
CPC .......... *G01N 33/68* (2013.01); *A01K 43/00* (2013.01); *G01N 30/72* (2013.01); *G01N 30/88* (2013.01); *G01N 33/08* (2013.01); *G01N 33/4833* (2013.01)

(58) Field of Classification Search
CPC .... G01N 33/68; G01N 30/88; G01N 33/4833; G01N 33/08; G01N 30/72; A01K 43/00
USPC ......................................................... 436/111
See application file for complete search history.

(56) References Cited

U.S. PATENT DOCUMENTS

| | | | |
|---|---|---|---|
| 5,158,038 A | 10/1992 | Sheeks et al. | |
| 5,575,237 A | 11/1996 | Ferguson | |
| 5,784,992 A | 7/1998 | Petitte et al. | |
| 6,029,080 A * | 2/2000 | Reynnells | G01R 33/483 600/407 |
| 6,240,877 B1 | 6/2001 | Bounds | |
| 6,286,455 B1 | 9/2001 | Williams | |
| 6,365,339 B1 | 4/2002 | Daum et al. | |
| 6,506,570 B1 | 1/2003 | Phelps | |
| 6,510,811 B1 | 1/2003 | Gore et al. | |
| 7,041,439 B2 | 5/2006 | Phelps et al. | |
| 7,418,922 B2 | 9/2008 | Wolfe et al. | |
| 8,624,190 B2 * | 1/2014 | Steiner | G01N 21/552 250/339.08 |
| 10,091,974 B2 * | 10/2018 | Sewiolo | A61B 5/055 |
| 2003/0096319 A1 * | 5/2003 | Phelps | A01K 43/00 435/7.2 |
| 2006/0160080 A1 * | 7/2006 | Clinton | C12Q 1/6879 435/6.12 |
| 2011/0144473 A1 | 6/2011 | Opitz et al. | |
| 2015/0260704 A1 * | 9/2015 | Bruins | G01N 33/50 435/235.1 |
| 2017/0205353 A1 | 7/2017 | Galli et al. | |
| 2019/0174726 A1 * | 6/2019 | Knepper | A61B 10/00 |

FOREIGN PATENT DOCUMENTS

| | | |
|---|---|---|
| CA | 2750877 A1 | 7/2010 |
| CN | 1232545 A | 10/1999 |

(Continued)

OTHER PUBLICATIONS

Ricks, C. A. et al., Poultry Science 2003, 82, 931-938.*

(Continued)

*Primary Examiner* — Arlen Soderquist (74) *Attorney, Agent, or Firm* — Nixon Peabody LLP; Ronald I. Eisenstein; Nicole D. Kling (57) ABSTRACT

The present invention relates to a method for non-destructively identifying a characteristic of a *Gallus Gallus domesticus* embryo in ovo, the method comprising: (a) obtaining a sample of material associated with an egg comprising the embryo, and (b) measuring a score value for the presence of, and concentration of at least a first biomarker in the sample indicative of the characteristic of the embryo, and (c) applying a threshold to the score value and concentration obtained in (b) to identify the characteristic for the embryo associated with the presence and concentration of the biomarker, wherein an at least first biomarker comprises an amino compound having a molecular weight in the range of from 140 to 190 g/mole, wherein step (c) further comprises: (i) correlating each relevant biomarker signal with a reference biomarker by matching the spectrum of each correlating signal with the expected spectrum of the correlating reference biomarker using a similarity measure, to define at least one positively correlating signal; (ii) measuring the intensity of each positively correlating signal and scoring its absolute and/or relative signal intensity; and (iii) applying a threshold to the score value obtained from a similarity function to determine the correlated embryo characteristic.

15 Claims, 3 Drawing Sheets

(56) References Cited

FOREIGN PATENT DOCUMENTS

| | | | |
|---|---|---|---|
| CN | 1313726 | A | 9/2001 |
| CN | 102210708 | A | 12/2011 |
| EP | 1543323 | A2 | 6/2005 |
| EP | 2369336 | A1 | 9/2011 |
| JP | 2009540319 | A | 11/2009 |
| JP | 2012042471 | A | 3/2012 |
| JP | 2012116665 | A | 6/2012 |
| JP | 2015523097 | A | 8/2015 |
| RU | 2406371 | C1 | 12/2010 |
| WO | 9814781 | A1 | 4/1998 |
| WO | 2002083848 | A2 | 10/2002 |
| WO | 2004016812 | A1 | 2/2004 |
| WO | 2007144606 | A2 | 12/2007 |
| WO | 2013021715 | A1 | 2/2013 |
| WO | 2014021715 | A2 | 2/2014 |
| WO | 2014116833 | A2 | 7/2014 |
| WO | 2016000678 | A1 | 1/2016 |

OTHER PUBLICATIONS

Weissmann, A. et al, Theriogenology 2013, 80, 199-205.*

Corion, M. et al, Poultry Science 2022, 101, paper 101782, 11 pages.*

Aslam et al. "Yolk concentrations of hormones and glucose and egg weight and egg dimensions in unincubated chicken eggs, in relation to egg sex and hen body weight" General and Comparative Endocrinology 187: 15-22 (2013).

Rupe et al. "Amino acid studies in the transformation of proteins of the hen's egg to tissue proteins during incubation." Journal of Biological Chemistry 213: 899-906 (1955).

Perederiy, "Methane from biomass," LesProminform 74(8); 164 (2010) found on Jun. 21, 2017, on Internet [online] https://lesprominform.ru/jarticles.html?id=21215 [Engligh Translation Included].

Sanitary Regulations and Standards 2.3.6.1079-01, Sanitary-epidemiological requirements to catering institutions, manufacturing and circulation of food products and food stock by them, Ministry of Health of the RF, Moscow, 2002, found on Jun. 21, 2017 on Internet [on-line] at http://www.gosthelp.ru/text/sanpin2361079o1sanitarnoe.html [English Translation Included].

Webster et al. "Avian egg odour encodes information on embroyo sex, fertility and development." PloS One 10(1): e0116345 pp. 1-10 (2015).

Beato et al., "Avian influenza viruses in poultry products: a review", Avian Pathol, 38(3): 193-200 (2009).

Chinese Office Action for Chinese Patent Application No. 201380046983.6 112013; English Translation.

International Search for WO 02/083848 (dated May 5, 2003).

Lu et al., "Development Changes of Plasma insulin, Glucagon, Insulin-like Growth Factors, Thyroid Hormones, and Glucose Concentrations in Chick Embryos and Hatched Chicks", Poultry Science 86; 673-683 (2007).

Ohta et al., "Embryo Growth and Amino Acid Concentration Profiles of Broiler Breeder Eggs, Embryos, and Chicks After in Ovo Administration of Amino Acids", Poultry Science, 80:1430-1436 (2001).

Roos Molenaar et al., "High Environmental Temperature Increases Glucose Requirement in the Developing Chicken Embryo", PLOS One 8(4):e59637 (2013).

Search Report and Written Opinion for Priorty Netherlands application NL2009256 (dated Feb. 6, 2013) and English translation of Part I, V + VIII of the Written Opinion.

Search Report and Written Opinion of Priority Netherlands application NL2009255 (dated Sep. 27, 2012) and English translation of Part I, V + VIII of the Written Opinion.

* cited by examiner

METHOD AND SYSTEM FOR THE NON-DESTRUCTIVE IN OVO DETERMINATION OF FOWL GENDER

CROSS REFERENCE TO RELATED APPLICATIONS

This application is a 371 National Phase Entry of International Patent Application No. PCT/NL2017/050330 filed on May 24, 2017 which claims benefit under 35 U.S.C. § 119(b) of NL Application No. 2016818 filed May 24, 2016, NL Application No. 2016819 filed May 24, 2016, and NL Application No. 2017382 filed Aug. 29, 2016, the contents of which are incorporated herein by reference in their entirety.

FIELD OF THE INVENTION

The present invention relates to a process for the non-destructive determination in ovo of the gender of an oviparian species, particularly of an avian species, more particularly of the *Gallus Gallus* species. The present process further relates to the selection of male eggs and female eggs, and to the production of groups of live animals using these selected eggs.

Oviparous animals lay eggs, with little or no other embryonic development within the mother. Cultivation of oviparian animals and their eggs caters for an ever growing part of the global protein supply, as well as for various other large scale industrial processes, such as production of vaccines. At present, the most important processes for the cultivation of oviparian animals include the rearing of avian species, such as poultry, and aquaculture, i.e. the farming of aquatic organisms such as fish, crustaceans and mollusks. In particular fowl, more specifically re jungle fowl chicken, i.e. of the species *Gallus Gallus Domesticus*, are by far the most reared oviparian species in the world.

BACKGROUND OF THE INVENTION

Fertilized chicken eggs tend to deliver an about equal distribution of male and female animals. However, for various reasons, in hatchery management, it may be desirable to separate animals based upon various characteristics, in particular gender. In commercial domestic chicken and egg production for instance, incubation and rearing of male chicks is highly undesirable, leading to the culling of billions of male chicks every year.

Currently, in both cases, mixed populations of hatched chicklets are subjected to sexing by visual assessment of the juvenile animal, of sometimes even the adult population in the cases where juveniles do not have suitable traits. In either case, this is a highly time consuming process, requiring highly skilled operators, and is typically very stressful for the animals.

Yet further, for commercial egg production, the incubation and rearing of male chicks is highly undesirable, leading to the culling of billions of male chicks every year. Furthermore, there is a percentage of eggs that are unfertilized, or do not comprise a viable embryo at the beginning of the incubation period, which greatly reduces the capacity of the incubators at hatcheries.

Also, where adult animals are sexed, the entire populations needs to be reared to a minimum age, while only half of the thus reared animals are used for proliferation after separation. Further problems may occur where the presence of e.g. a male population may lead to reduced productivity due to e.g. cannibalism and reduced farming density.

Furthermore, there is a percentage of eggs that are unfertilized, or do not comprise a viable embryo at the beginning of the incubation period, which greatly reduces the capacity of the incubators employed at hatcheries, in particular for poultry eggs.

As a result, an incubation capacity is required which is at least twice as large as necessary if an early gender selection would be available, permitting the selection of primarily only male or female embryos.

Accordingly, it would be of great value for the environment, by reduction of the amount of energy and other resources required, but equally for the elimination of unnecessary animals by culling, as well as reduction of stress for the newly hatched animals, if an early stage method was available that allowed to determine the gender of avian embryos prior to the incubation phase, also permitting to strongly increase the capacity of hatcheries. A further benefit would be if the method also permitted to select viable embryos over unfertilized and/or otherwise nonviable eggs, increasing the efficiency of the hatching process further.

There are various methods disclosed in the literature relating to determinations of the gender of an avian embryo through detection of certain metabolites in the eggs, e.g. through NMR spectroscopy, e.g. Y. Feng et al., Appl. Magn. Reson. (2007), 32, 257-268; by HPLC analysis, see Gu D.-C. et al., Chinese Journal of Animal Science, Vol. 7, 23-25), and through the use of biomarker specific binding target molecules that allow for quantitative fluorescence microscopy, see for instance WO2006/124456 for the determination of the presence of an estrogenic steroid compound as marker. It is generally noted that steroids are rather large molecules, which are not easily volatized.

A disadvantage of most methods mentioned herein above is that they are not able to allow for the non-destructive determination of the gender of a chicken, as larger quantities of metabolites are required which may not allow an embryo to subsist and fully develop once a sample has been taken. Also, the methods require the use of equipment which is not typically employed at a chick farm due to cost or complexity, let alone offering an appropriate throughput for commercial chicken rearing.

WO2014/021715 discloses a process for the non-destructive determination of gender, developmental stage and/or viability of an avian embryo in an egg, comprising (a) detecting at least a first developmental marker compound selected from sugars and/or amino acids, precursors and metabolites thereof in an egg at a time period of from the beginning of the incubation of the egg until the hatching; (b) measuring the amount of the at least first detected developmental marker compound, and (c) comparing the amount to a base line established for male and female, developmental stage of the embryo, and/or alive and deceased or non-developed embryo, to determine whether the embryo is viable, male or female, and/or the developmental stage of the embryo. While the disclosed method is very useful for the determination of the gender, age and developmental stage of the embryo, it requires relatively large amounts of samples due to the low sensitivity of some of the quantitative measurement methods. Also, some of the automated methods are difficult to implement in a real-time continuous hatching process, e.g. using nuclear resonance methods or spectral resonance methods including Raman spectroscopy. Other methods, while fast, require the presence of relatively expensive equipment, and/or use of specialty chemicals such as fluorescence markers for specific biomarker molecules.

Hence there remains a need for a faster, and more sensitive method for the non-destructive determination of gender, as well as developmental stage and/or and viability of an oviparian animal embryo in ovo.

SUMMARY OF THE INVENTION

It is therefore an object of the present invention to provide a method for non-destructively identifying a characteristic of a *Gallus Gallus domesticus* embryo in ovo, the method comprising:
(a) obtaining a sample of material associated with an egg comprising the embryo, and
(b) measuring a score value for the presence of, and concentration of at least a first biomarker in the sample indicative of the characteristic of the embryo, and
(c) applying a threshold to the score value and quantity obtained in (b) to identify the characteristic for the embryo associated with the presence and concentration of the biomarker,
wherein an at least first biomarker comprises an amino compound having a molecular weight in the range of from 140 to 190 g/mole, and wherein the presence and concentration of the biomarker correlates to an embryo being likely to develop into a male adult, or into female adult.

It is yet a further object to provide a system capable of performing real time online analysis of eggs at remote locations, such as hatcheries or aquacultures. These and other objects are addressed by the apparatus and process of the present invention.

In a further aspect, the subject process also relates to a multitude of viable female eggs, forming a predominantly male or predominantly female egg selection. In yet a further aspect, the subject process also relates to a juvenile animal population obtainable by the method according to the invention. In yet a further aspect, the subject process also relates to the use of a multitude of eggs obtainable from the process for animal and/or human food production, for the production and/or isolation of cosmetic, medical and/or nutritional compounds, for methane production through fermentation, vaccine production, and/or high quality fertilizer production.

In yet a further aspect, the subject process also relates to an oviparian animal embryo gender detection and analysis system, comprising a preferably fully automated apparatus for the execution of the subject methods.

The present invention also relates to the system, wherein the gender identification facility is implemented in software on an electronic device interfaced with the spectroscopic system; and preferably wherein the identification facility comprises software means resident in a computer.

SHORT DESCRIPTION OF THE FIGURES

The present invention now is described more fully hereinafter with reference to the accompanying drawings, in which a preferred embodiment of the invention is shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

DETAILED DESCRIPTION OF THE INVENTION

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The terms "avian" and "bird" as used herein, include males or females of any avian species, but are primarily intended to encompass poultry which are commercially raised for eggs or meat. Accordingly, the terms "bird" and "avian" are particularly intended to encompass red and grey jungle fowl, chicken, turkeys, ducks, geese, quail, doves, ostrich, emu, and pheasants.

The term "incubation" herein refers to the process by which birds hatch their eggs, and to the development of the embryo within the egg after leaving the hen's tract. The incubation period herein refers to the uninterrupted time during which a particular egg is subjected to conditions emulating the brooding until the hatching, i.e. emergence of the birds, including any handling or transfers from e.g. an incubator to a hatchery unit, provided the development of a bird is not stalled.

The term "in ovo" as used herein, refers to embryos contained within an egg prior to hatch. The present invention may be practiced with any type of bird, including, but not limited to, (domesticated) chicken, turkey, duck, goose, quail, and pheasant eggs.

The terms "injection" and "injecting" herein encompass methods of inserting a device (typically an elongate device) into an egg or embryo, including methods of delivering or discharging a substance into an egg or embryo, methods of removing a substance (i.e., a sample) from an egg or embryo, and/or methods of inserting a detector device into an egg or embryo.

The term "mass spectrometry" herein refers an analytical technique that sorts ions based on their mass. Mass spectrometry typically is used for chemical analysis in many situations and might be applied to any sample from a complex mixture of petroleum to the products of genetic engineering. In simple terms, a mass spectrum will give a picture of the exact chemical composition of a sample.

The present application, in a first aspect, relates to the determination of one or more amino compounds having a molecular weight in the range of from 140 to 190 g/mole, preferably of from 150 to 170 g/mole.

Applicants surprisingly found that a specific metabolite, a structural isomer of ethionine, is indicative of whether an embryo will develop into a male or female hatchling. Preferably, the biomarker compound is of formula $R^3SCR^1HCR^2HCOOH$ (I), wherein preferably, $R^1$ represents $CH_3$, H, $NH_2$, $R^2$ represents $CH_3$, H, $NH_2$, and $R^3$ represents —$(CH_2)_2$—$NH_2$, or structural isomers thereof. More preferably, the biomarker compound is of formula $C_6H_{13}NO_2S$. More preferably, it may advantageously be selected from amino acids such as 2-amino-4-ethylsulfanylbutanoic acid (also referred to as Ethionine), or structural isomers thereof, including, but not limited to 4-(Methylsulfanyl)isovaline, 4-(Methylsulfanyl)isovaline (also known as 2-amino-2-methyl-4-(methylsulfanyl)butanoic acid), N- or Isopropylcysteine, 3-(Methyl-sulfanyl)valine, 4-(Methylsulfanyl)valine, 3-Methyl-3-sulfanyl-isovaline, 4-(Methylsulfanyl)isovaline, 2-Amino-3-methyl-4-methylsulfanyl-butyric acid, 5-(Methylsulfanyl)norvaline, 2-Amino-3-methyl-3-sulfanylpentanoic acid, Methyl 3-sulfanyl-valinate, Methyl Sulfonium Methionine, N-Methyl-D-methionine; 5-amino-6-sulfanylhexanoic acid, or the like; from amino acid esters such as Methyl 2-amino-4-methylsulfanyl)butanoate (also known as methyl methioninate), or structural isomers thereof, such as Ethyl methyl-cysteinate, Isopropyl-cysteinate, N-Propyl cysteinate, or related compounds such as 2-[(2-Hydroxyethyl)sulfanyl]-N-methylpropanamide; Ethyl homocysteinate, 2-Isopropyl-1,2-thiazolidine 1,1-dioxide, 1-amino-2,2-diethoxyethane-1-thione, 3-[(2-hydroxyethyl)sulfanyl]-N-methylpropanamide, propyl 2-amino-3-sulfanylpropanoate, 2-(methylamino)-4-(methylsulfanyl)butanoic acid, 2-[(2-aminoethyl)sulfanyl]-2-methylpropanoic acid, 3-[(2-aminoethyl)sulfanyl]-2-methylpropanoic acid, 3-[(2-aminoethyl)sulfanyl]butanoic acid, 4-[(2-aminoethyl)sulfanyl]butanoic acid, 2-amino-3-(propylsulfanyl)propanoic acid, 2-amino-3-(propan-2-ylsulfanyl)propanoic acid, and 3-[(2-aminoethyl)sulfanyl]butanoic acid. The compounds or isomers may be racemic, or may comprise enantiomers or stereoisomers in suitable ratios and amounts.

Preferably, the compound has molecular formula $C_6H_{13}NO_2S$, and a Monoisotopic mass $M_w$ of 163.0690. At present, it appears to be identified as (3-[(2-aminoethyl)sulfanyl]butanoic acid), having the a structure according to general formula I:

Applicants found that the concentration of compound (I), or a structural isomers, which may be considered as a non-proteinogenic amino acid, in the allantoic fluid during the incubation period may be advantageously used to determine the sex of the embryo in the egg, with a very high certainty. As an additional benefit, this biomarker is comparatively easy to extract and/or volatize, and hence may be analyzed with comparative ease as compared to for instance steroidal compounds.

Step (a) comprises obtaining a sample of material associated with an egg comprising the embryo.

Methods and apparatus according to embodiments of the present invention may be utilized for identifying one or more characteristics of an egg at any time during the embryonic development period, also referred to as the incubation period thereof. Embodiments of the present invention are not limited to a particular day during the embryonic development period.

The process according to the present invention preferably comprises (a1) providing a sample comprising an egg fluid; and (a2) acquiring the spectrum from the sample. Optional step (a3) removes preferably turbidity from the samples, by a suitable method such as ultrafiltration or centrifugation. As set out above, while the invasive methods permit to take a sample directly, and to subject the sampled fluid to an analysis, preferably the analysis is performed non-invasively due to the efficiency of such analysis method, and to the fact that the eggshell and membranes therein remain imperforated. Any suitable method may be employed to perform such non-invasive analysis.

Where a non-invasive method is to be employed, the term "fluid" herein may refer to volatile compounds that can be removed from the egg without piercing the egg shell. This may advantageously be performed by placing an egg in a detection chamber, optionally under slight under-pressure, and by submitting released volatile compounds to a suitable identification and quantification method. Here, the above cited Mass Spectroscopic (MS) methods may be applied, including the use of an Ion Mobility Spectrometer (IMS).

If the analysis is performed invasively, this typically includes the extraction of a sample of egg material. The sample is preferably taken from an embryonic fluid, preferably from the allantoic fluid in the case of avian species, since this will least likely harm the embryo. The allantoic fluid typically is an excretory medium for the nitrogenous metabolites of an avian embryo.

Suitable methods and apparatus for the penetration of eggs and invasively sampling of egg material are disclosed for instance in US-A-20070137577, WO-A-00/22921 or WO-A-99/34667. The thus taken sample is then preferably subjected to a suitable protocol to permit the detection of the developmental markers, and an analysis of the relative and/or absolute amounts of developmental markers present.

The allantoic fluid begins to form around day 3 of incubation, as disclosed by Hamburger, V and Hamilton, H L (1951). "A series of normal stages in the development of the chick embryo". Journal of Morphology 88 (1): 49-92. Herein is indicated that the allantois was distinguishable at 65 hours after incubation, as a short, thick-walled pocket; not yet vesicular. After 72 hours, the allantois was vesicular, variable in size; on the average of the size of the midbrain, indicating that the allantois and the allantoic fluid are present as of day 3. As a result, the present method may be applied as of day 3 if allantoic fluid is to be examined.

The allantois attains a maximum volume on about day 13 of incubation and then wanes in volume as incubation continues due to moisture loss and fluid resorption, but is still present in significant volumes on day 18 of incubation.

The allantoic fluid is separated from the eggshell by the inner and outer shell membranes and the chorioallantoic membranes. Although the allantoic fluid encompasses the entire periphery of an embryonated egg, the allantoic fluid typically accumulates at the top of an egg directly underneath the membranes overlying the air cell.

The accumulation of the allantoic fluid at the top of the egg is due to gravity and displacement by the dense embryo and yolk sac. Attempting to accurately sample the allantoic fluid through the top of an egg while the egg is upright may be difficult due to the variability of the air space from egg to egg. Gravity can be used to pool the allantoic fluid in a localized site. When an egg is turned on its longitudinal axis, the allantoic fluid will pool at the top side of the egg, directly underneath the shell. Laying the egg on its longitudinal axis renders the allantoic fluid useful for extraction of a sample.

The extraction of material, such as allantoic fluid, from eggs may be performed in various ways, including penetrating the egg shell, and inserting a sampling cannula trough the membranes. A sample of the fluid to be sampled may then be retrieved, while the membrane and/or shell is actively sealed with a suitable sealant, or allowed to seal itself.

As stated above, any suitable method may be employed to perform a non-invasive analysis. In a different preferred embodiment of the present, noninvasive method may involve solid-phase microextraction (SPME), coupled with a suitable analytical apparatus. SMPE refers to a solid phase extraction sampling technique that involves the use of a fiber coated with an extracting phase, that can be a liquid (polymer) or a solid (sorbent), which extracts different kinds of analytes (including both volatile and non-volatile) from different kinds of media, that can be in liquid or gas phase. The quantity of analytes extracted by the fiber is proportional to its concentration in the sample as long as equilibrium is reached or, in case of short time pre-equilibrium, with help of convection or agitation. This may preferably be coupled with an IMS, so that the volatiles can be directly measured.

While several publications have generally disclosed the use of non-invasive methods, e.g. US-A-2011/144473 and U.S. Pat. No. 7,950,349, these publications only vaguely describe overall emission spectra; which in practice do not permit to select the gender of an embryo. The present process differs in particular from the disclosed methods in that the presence of specific components in the egg is determined, which may advantageously be done by using secondary derivative spectra that allow to selectively seek for the absolute and relative amounts of one or more developmental marker compound(s).

Eggs comprising male and female embryos exhibit differences in chemical composition at the molecular level. At the macroscopic level, the embryos also show differences in size, shape and cell morphology.

The present process advantageously permits to determine the gender of an embryo. Preferably the determination is performed at a period of from 1 to 15 days, more preferably of from 2 to 14, yet more preferably of from 3 to 13, and even more preferably of from 4 to 12 days after the incubation is started, such as performing step a) preferably at a time period of from 6 to 12 days after the beginning of the incubation of the egg.

This permits to avoid the costs involved in incubating eggs that are either no viable and/or not the desired gender. Furthermore, the actual developmental stage of an egg can be determined. For species with shorter or longer incubation times than those of domesticated chicken, other periods may apply, as suitable.

The sample may be any biological substance of interest, but is advantageously a biological tissue and preferably a biological fluid such as blood or plasma.

Step (b) comprises measuring a score value for the presence of, and concentration of at least a first biomarker in the sample indicative of the characteristic of the embryo.

The method of the invention relies upon correlation of observed mass signals with reference masses and spectra of known biomarkers. The reference data is preferably stored on a computer server, which allows the entire procedure to be carried out under computer control. Signals are correlated to reference standards by comparison, for example using computational functions as described herein.

Preferably, signals are characterized as "positive" or "negative" according to whether a threshold level of similarity is achieved; signals which are negative and do not achieve the threshold level of similarity are discarded in the process, whilst those signals which are positive are matched with biomarkers and result in a diagnosis of the presence of said biomarkers in a biological sample.

In the case of implementation with standards, the scoring of the biomarker signals may be calculated by the ratio between the signal of biomarker present in the sample and the internal standard added to the sample. Multiple biomarkers may be analyzed the same way resulting in a final scoring factor.

Preferably, one or more internal standards of reference biomarkers labelled with an atomic tag are added to the sample prior to analysis by mass spectrometry. This permits to determine, and score the absolute signal intensity by measuring the biomarker signal intensity and comparing it to the signal intensity of one or more known internal standards. Such standards may for instance be labelled with an isotope, making the assay read-out highly accurate in terms of, as well advantageous in terms of absolute quantitation. Built in calibration sequences within the screening will allow the measurement of absolute biomarker levels in a sample.

The method of the invention may preferably be implemented in two ways; using internal standards to provide a reference for quantitating signal intensity, and without such standards. Thus, in one embodiment, one or more internal standards are added to the sample prior to analysis by mass spectrometry. Preferably, the internal standards are labelled. Advantageously, the absolute signal intensity for each biomarker signal may then be scored by measuring the biomarker signal intensity and comparing it to the signal intensity of one or more known internal standards. In the alternative implementation, the sample is processed without the addition of internal standards. In such an embodiment, the relative signal intensity is scored by measuring the ratio between the individual biomarker signal intensities in a sample and the reference signal intensity for a sample group.

Preferably, a selected characteristic may be the likely viability or non-viability of an embryo to achieve full growth to hatching. A further preferred selected characteristic is a prognosis for the likely developmental stage and time required for the embryo to progress to hatching under incubation conditions. Preferably the method comprises applying one or more of a magnetic resonance imaging method; a spectral resonance method; an analytical chromatographic method coupled with one or more suitable detectors; fluorescence spectroscopy; and/or assay methods comprising biomarker selective reagents.

The identification and quantification of the one or more biomarkers may be performed by any suitable method. Advantageously this may be performed by a magnetic resonance imaging method including nuclear resonance methods; spectral resonance methods including UV/VIS, infrared or Raman spectroscopy; analytical methods such as GC or HPLC coupled with suitable detectors; fluorescence spectroscopy; enzyme-linked immunosorbent assays, including wet and dry methods, such as using a dipstick method; and the use of suitably prepared selective aptamers or similar selective reagents.

Typically, also quantitative spectral resonance methods including infrared or Raman spectroscopy may be employed, preferably using secondary spectra for the determination of the presence and absolute and/or relative amounts of developmental markers present in an egg. While several publications have disclosed the use of non-invasive methods, e.g. US-A-2011/144473 and U.S. Pat. No. 7,950, 349, these publications only vaguely describe overall emission spectra; which in practice do not permit to select the development stage the viability and/or the gender of an embryo. The present process differs in particular from the disclosed methods in that the presence of specific components in the egg is determined, which may advantageously be done by using secondary derivative spectra that allow to selectively seek for the absolute and relative amounts of one or more developmental marker compound(s). In particular differential second-derivative Fourier transform infrared (FTIR) and FT-Raman spectroscopy, or combination thereof may advantageously be employed to achieve the necessary accuracy and repeatability, while nuclear magnetic resonance methods may suitably be employed to determine the nature of the developmental markers, and to establish a base line to calibrate the system. The present process advantageously permits to determine the viability, and/or gender of an embryo, and/or preferably the developmental stages from the beginning of the incubation of the egg until the hatching. In a preferred embodiment, the sample may be analyzed by any mass spectrophotometric method suitable to detect and to acquire a spectrum that identifies and quantifies the absolute and relative amount of biomarkers present in the sample. Preferably, the sample may be analyzed by a method that permits real-time analysis in less than 20 seconds, more preferably less than 15 second per sample, Examples include direct infusion using static nano-electrospray principles, flow injection analysis or flow injection with sample enrichment. Preferably, the mass spectrometric analysis comprises electrospray ionisation (ESI) mass spectrometry, matrix-assisted laser desorption ionisation-time of flight (MALDI-TOF) mass spectrometry or surface enhanced laser desorption ionisation-time of flight (SELDI-TOF) mass spectrometry. The mass spectrometer preferably operates in a tandem and/or survey mode.

Advantageously, the sample may be processed prior to mass spectroscopic analysis, such that the sample processing comprises sample separation by solid phase extraction (SPE), gas chromatography, single- or multi-phase high-pressure liquid chromatography (HPLC).

Alternatively, if the biomarker compounds can be measured externally, a direct, non-invasive analysis through direct, non-invasive measurements on entire eggs may be performed, using for instance the IMS technology set out above.

Preferred methods for the mass spectrometric characterization of biomarkers include matrix-assisted laser desorption ionization (MALDI) and electrospray ionization (ESI). Either may advantageously be can be combined with time-of-flight (TOF) or other types of mass spectrometric sensors to determine the mass and/or fragmentation pattern of a biomarker. Preferably, mass spectrometry may be employed in tandem with chromatographic and other separation techniques herein. MALDI operates by pulsing a sample with lasers. This treatment vaporizes and ionizes the sample. The molecular weights (masses) of the charged ions are then determined in a TOF analyzer. In this device, an electric field accelerates the charged molecules toward a detector, and the differences in the length of time it takes ionized fragments to reach the detector, i.e. their time-of-flight, to reveal the molecular weights of the biomarkers, whereby smaller compounds reach the detector earlier. This method generates mass profiles of the sample—that is, profiles of the molecular weights and amounts of compounds in the mixture. These profiles can then be used to identify known biomarkers from biomarker databases.

With an ESI-MS interface to liquid chromatography (LC/MS/MS), the eluting compounds from the LC-column are introduced into the ion source of the mass spectrometer. A voltage is applied to a fine needle. The needle then sprays droplets into a mass spectrometric analyzer where the droplets evaporate and biomarker ions are released corresponding to a variety of charge states that are fragmented and from where the composition can be determined. Alternatively, SPE (solid phase extraction), or gas chromatography can be coupled with the Mass spectrometer.

In particular SPE/MS/MS was found useful for automated and high throughput industrial application of the present method, such as using an Agilent Rapidfire MS apparatus (Rapidfire is a registered trade mark of Agilent Inc.); a Phytronics The LDTD (Laser Diode Thermal Desorption) Ion Source (LDTD is a registered trade mark of Phytronics Inc.).

A further useful apparatus was found to use a calibrated Ion Mobility Spectrometer (IMS), based on the gas phase mobilities of ions in an electric field. Herein, the ions of a substance generated due to partial discharge, UV lamp or a $^{63}$Ni source inside a so-called ionisation chamber are separated from one another on their way through a drift tube according to their molecular mass and/or geometric structure. The apparatus then measures the characteristic drift times of the ions through this tube, allowing a rapid detection, identification as well as quantification of the substance, with an extremely high sensitivity, and within a few seconds per sample.

Preferably, the mass spectrometric analysis comprises electrospray ionisation (ESI) mass spectroscopy, matrix-assisted laser desorption ionisation-time of flight (MALDI-TOF) mass spectroscopy or surface enhanced laser desorption ionisation-time of flight (SELDI-TOF) mass spectroscopy, SPE/MS/MS, LDTD (Laser Diode Thermal Desorption) Ion Source, and/or use of an Ion Mobility Sensor (IMS).

The mass spectrometer system is preferably an electrospray ionisation (ESI) MS, matrix-assisted laser desorption ionisation-time of flight (MALDI-TOF) MS or surface enhanced laser desorption ionisation-time of flight (SELDI-TOF) MS, or Laser Diode Ionisation Desorption (LDID) MS. In particular SPE/MS/MS was found useful for automated and high throughput industrial application of the present method, such as using an Agilent Rapidfire MS apparatus (Rapidfire is a registered trade mark of Agilent Inc.); a Phytronics The LDTD (Laser Diode Thermal Desorption) Ion Source (LDTD is a registered trade mark of Phytronics Inc.).

A further useful apparatus was found to use a calibrated Ion Mobility Spectrometer (IMS), based on the gas phase mobilities of ions in an electric field. Herein, the ions of a substance generated due to partial discharge, UV lamp or a $^{63}$Ni source inside a so-called ionisation chamber are separated from one another on their way through a drift tube according to their molecular mass and/or geometric structure. The apparatus then measures the characteristic drift times of the ions through this tube, allowing a rapid detection, identification as well as quantification of the substance, with an extremely high sensitivity, and within a few seconds per sample.

Preferably, the test sample may be processed prior to analysis. Preferably, the sample processing comprises sample separation by solid phase extraction (SPE), gas chromatography, single- or multi-phase high-pressure liquid chromatography (HPLC). Preferably, one or more internal standards of reference biomarkers are added to the sample prior to analysis. Preferably, the absolute signal intensity is scored by measuring the biomarker signal intensity and comparing it to the signal intensity of one or more known internal standards. Preferably, the method is fully automated.

Preferably, a multitude of eggs are examined for one or more embryonic characteristics.

Preferably, the method further comprises determining whether an embryo in an egg is viable and male, or viable and female, or non-viable, and separating a multitude of viable male eggs from a multitude of viable female eggs, and one or more non-viable eggs.

Preferably, the method further comprises identifying at least one biomarker from the plurality of biomarkers from the sample and comparing the concentration of the at least one biomarker with the values of the same biomarker in individual chicken embryos with known characteristics, wherein the higher or lower concentration with regard to a threshold of the one or more biomarkers is an indication of the embryo being male or female, viable or non-viable, and/or the developmental stage of the embryo.

Step (c) comprises applying a threshold to the score value and quantity obtained in (b) to identify the characteristic for the embryo associated with the presence and concentration of the biomarker. Preferably, step (c) further comprises: (i) correlating each relevant biomarker signal or signature with a reference biomarker by matching the spectrum of each correlating signal with the expected spectrum of the correlating reference biomarker using a similarity measure, to define at least one positively correlating signal; (ii) measuring the intensity of each positively correlating signal and scoring its absolute and/or relative signal intensity; and (iii) applying a threshold to the score value obtained from a similarity function to determine the characteristic for the embryo associated with the presence and concentration of the correlated biomarker.

Applicants found that the presence of 3-[(2-aminoethyl)sulfanyl]butanoic acid in an amount of 50 ng/ml or more in the allantoic fluid on day 7, 8 or 9 correlates to a female embryo, while a presence of the biomarker present in less than 50 ng/ml correlates to a male embryo. Preferably, 3-[(2-aminoethyl)sulfanyl]butanoic acid is present in an amount of from 0.1 to 45 ng/ml, more preferably in an amount of from 1 to 40 ng/ml in male eggs on day 7, 8 or. Preferably, 3-[(2-amino-ethyl)sulfanyl]butanoic acid is present in an amount of from 50.1 to 150 ng/ml, more preferably in an amount of from 55 to 140 ng/ml in female eggs on day 7, 8 or 9.

While this single biomaker already may give almost complete certainty on the desired characteristic, at least a first and a second biomarker, or even more biomarkers may advantageously be detected and analyzed simultaneously. The absolute and/or relative amounts of the at least first and second markers may then be employed to determine the one or more characteristics with an even increased certainty.

The present invention also preferably relates to a process for the selective incubation of hatchlings of a oviparian species with a specific characteristic, comprising providing a multitude of eggs from the species, and subjecting the eggs to the method disclosed herein, to determine a characteristic of the embryo, and selecting the eggs with the desired characteristic to form a selected multitude of eggs, and incubating the selected eggs until one or more of the hatchlings hatch.

The present invention also preferably relates to an oviparian species embryo gender detection and analysis system, comprising:
  (i) a sample taking system for taking samples from individual eggs;
  (ii) an analytical system for collecting spectra;
  (iii) a gender and/or viability identification facility programmatically identifying signals associated with one or more biomarkers from one or more samples analyzed by the analytical system, the facility further performing an analysis comparing the signals with a stored library of control spectra collected on the sample data and/or with an internal standard, to identify the embryonic characteristic; and
  (iv) an output means coupling the one or more embryonic characteristic information to a sample and/or an analyzed egg.

Preferably, the identification facility is implemented in software on an electronic device interfaced with the analytical system.

The present invention also preferably relates to the use of a multitude of eggs obtainable from the method according to the invention for animal and/or human food production, for the production and/or isolation of cosmetic, medical and/or nutritional compounds, for methane production through fermentation, and/or high quality fertilizer production.

The term "allantoic fluid" herein encompasses allantoic fluid with or without the presence of other egg materials as derived from avian eggs. For example, the term allantoic fluid may include a mixture of blood and allantoic fluid. Embodiments of the present invention are not limited to extracting material from the allantoic fluid or from areas near the upper surface of an egg. Removal of material from the allantoic fluid as described herein is provided as merely one example of possible embodiments of the present invention. Various materials including but not limited to amnion, yolk, shell, albumen, tissue, membrane and/or blood, may be extracted from an egg and assayed to submit to a spectrophotometric analysis, to identify the gender of the embryo, as described below.

Where desired, material may be extracted from eggs having virtually any orientation. The term "predetermined location" herein indicates a fixed position or depth within an egg. For example, a device may be injected into an egg to a fixed depth and/or fixed position in the egg. In alternative embodiments, the injection may be carried out based on information obtained from the egg, e.g., regarding the position of the embryo or the subgerminal cavity within the egg.

In the present process, the developmental markers may preferably be analyzed invasively or non-invasively.

Preferably the determination is performed at a period of from 1 to 15 days, more preferably of from 2 to 14, yet more preferably of from 3 to 13, and even more preferably of from 4 to 12 days after the incubation is started, such as for instance performing step a) preferably at a time period of from 6 to 12 days after the beginning of the incubation of the egg. Furthermore, the actual developmental stage of an egg can be determined Preferably the determination of the embryo characteristic according to the present invention is performed as a non-destructive method, i.e. allowing the thus tested embryos to grow, if so desired, or to subject it to further steps such as in ovo vaccine production, provided the embryo is viable, or to grow the male eggs to an exclusively male population of chicken, for instance for meat production, or to use the thus reared chicks for other purposes.

The term "comparing the spectra" advantageously may include a univariate or preferably multivariate analysis of the measured spectra, and a determination of the association of an avian embryo with a certain population. The step may comprise determining the presence of certain signal peaks in the spectrum by multivariate statistical analysis of the spectral data. The multivariate statistical analysis program preferably comprises a principal components analysis program, and/or a partial least-squares regression analysis program.

The subject invention thus also pertains to a process, apparatus and system for determination of gender and/or viability of an avian embryo in ovo, comprising multivariate statistical analysis program, as well as a microprocessor implemented process for the determination thereof. Preferably, step (b) further comprises the step of normalizing intensity effects due to a concentration difference between any two samples.

Accordingly, the comparison preferably comprises an estimation of the likelihood of a gender for a sample using multivariate analysis of the measured spectra, and a determination of the association of an avian embryo with a certain population. Advantageously, this is performed using Partial Least Squares Discriminate Analysis (PLS-DA). The process preferably includes the mathematical treatment of the tracer compound data and includes a multi-variate analysis such as PCA (Principle Component Analysis), preferably followed by a supervised analysis, more preferably PLS-DA (Partial Least Squares-Discriminate Analysis) or even more preferably Orthogonal PLSDA, or similar suitable statistical approaches. The pattern matching step within the subject process will identify a certain similarity measure. Using the similarity measure, the correct structure of the biomarker is confirmed. This confirmation is made by spectral matching. The spectral matching is performed by comparison of the sample spectra and the reference spectra in the database. For a positive identity at this stage suitable correlation is required in order to confirm the accurate determination. Suitable threshold values and similarity measures will be apparent to those skilled in the art. This process attempts to reduce large amounts of data to a manageable size and apply a statistically driven model in order to determine latent variables indicative of hidden relationships between the observed data.

The Characteristic Identification facility then filters the sample data, which will identify clusters of interest among the samples. The clusters represent similarities among the samples and are used to identify the gender profiles. Preferably the analysis includes Principal Component Analysis (PCA) and PLS-DA. PCA employs mathematical algorithms to determine the differences and similarities in a data set. PCA transforms a number of possibly related variables into a smaller number of unrelated variables which are referred to as principle components. The first principle component accounts for as much of the variability in the data as possible. Each additional component attempts to account for as much of the remaining variability in the data as possible. The collected data may be arranged in a matrix and PCA solves for "eigenvalues" and "eigenvectors" of a square symmetric matrix with sums of squares and cross products. The eigenvector associated with the largest eigenvalue has the same direction as the first principle component. The eigenvector associated with the second greatest eigenvalue determines the direction of the second principle component. The sum of the eigenvalues equals the trace of the square matrix and the maximum number of eigenvectors equals the numbers of rows (or columns) of this matrix. Once determined, it is possible to draw screen plots of the calculated eigenvalues. Those skilled in the art will recognize that a number of different algorithms may be used to calculate the eigenvalues and eigenvectors. The data is displayed using two plots: i) the scores plot which shows the group clustering and ii) the loadings plot in which the spectral data responsible for the group clustering are identified as those being the greatest distance from the origin.

The present method advantageously may determine whether an embryo in an egg is viable and male, or viable and female, and to separate the tested eggs into a multitude of viable male eggs from a multitude of viable female eggs, and a multitude of non-viable eggs, to form a predominantly male or predominantly female egg, or predominantly non-viable egg selection. If so desired, the viable female or male egg selections may be subjected to incubation and the hatching process, to form a predominantly female or male animal population.

Eggs may be used for various applications, such as e.g. for vaccine production, by preferably injecting a virus or virus-like material into each egg identified as containing a live embryo and male or female. Then, after suitable incubation of the thus injected eggs, a vaccine or vaccine basis material may be isolated from the incubated eggs. An additional preferred embodiment of the present invention is a method for detecting the presence of a substance in an egg fluid sample, whereby a sample in the range of generally 0.1 to 35 µl may suffice.

The similarity measure preferably involves correlating retention index and fragmentation pattern associated with a positively correlated signal.

Further, statistically significant similarities may be detected and registered as relevant biomarker identities, or multiple biomarker identities. Determining statistically significant similarities involves using data bases as well as algorithms developed to meet the demands of the methodology.

This may include, in particular when determining the usefulness of a biomarker for a new species applying a supervised multivariate analysis, preferably Partial Least Squares Discriminate Analysis, PLS-DA or Orthogonal Partial Least Squares Discriminate Analysis to the data.

Preferably, the characteristic that is to be determined comprises gender, age, developmental stage and/or viability of the embryo in the egg. For industrial application, a multitude of eggs are examined for one or more embryonic characteristics.

The present method is preferably fully automated, thereby providing an assay for biomarkers in a sample associated with an egg which is automated and accurate. The assay thus relies on mass spectrometry to identify biomarkers. Advantageously, the method filters and screens mass and identities of data sets that are based on each of the unique properties of charge, mass, and fragmentation pattern associated with certain identified biomarkers in the sample.

By correlating the analysis of the tracer compound data with a library of samples of known gender, the selectivity of the determination of gender may advantageously be improved further. The present process further advantageously comprises determining whether an embryo in an egg is viable and male, or viable and female, and also permits to separate a multitude of viable male eggs from a multitude of viable female eggs, to form a predominantly male or predominantly female egg selection. The thus formed viable female or male egg selections may advantageously be subjected to an incubation and hatching process to form a predominantly female or male chick population.

The method according to the invention allows to analyze, simultaneously, hundreds or thousands of eggs, and hundreds or thousands of biomarkers in a sample taken from each egg. The method relies on a database of biomarkers, which have been shown to be associated with a characteristic, comprising mass and spectral data for each of the biomarkers and allows the biomarkers to be identified precisely by suitable software in a given sample.

Additionally, a database may be established for a certain species by screening the biomarkers present in a sample and eliminating undesired signals on the basis of the retention time index, which correlates with the time of arrival of the compound at the mass detector. Hence many sequences can be analyzed in minutes and given biomarkers identified with high confidence. The method is hence automatable, high-throughput and operable by relatively unskilled technicians, and therefore suitable for use at remote locations, e.g. hatcheries and chicken or fish farms.

The sample can be subjected to mass analysis without prior separation procedures. In such an embodiment, the sample is preferably analyzed by direct infusion using e.g. static nano-electrospray principles, flow injection analysis or flow injection with sample enrichment.

Advantageously, the sample is processed prior to mass analysis, preferably to separate sample components prior to loading them into the mass spectrometer. For example, the sample processing comprises sample separation by single- or multi-phase high-pressure liquid chromatography (HPLC), gas chromatography (GC), or solid phase extraction (SPE).

The mass spectrometer system is preferably electrospray ionization (ESI) MS, matrix-assisted laser desorption ionization-time of flight (MALDI-TOF) MS or surface enhanced laser desorption ionization-time of flight (SELDI-TOF) MS, or Laser Diode ionization Desorption (LDID) MS.

The method according to the invention is advantageously automated and performed under computer control. Identification of biomarkers in a sample is made by comparison with reference data for the biomarkers; preferably, reference mass and spectral data for a plurality of biomarkers are stored on a computer. Reference mass spectra for a defined biomarker are preferably averaged spectra obtained from actual and measured data obtained by a clustering calculation, as set out below. A biomarker can be relevant taken alone, in combination with other markers, for a characteristic that is objectively measured and evaluated as an indicator of a condition, such as gender, age and viability, or nourishment status. A useful biomarker may be any identifiable and measurable indicator associated with a particular condition or disease where there is a correlation between the presence or level of the biomarker and some aspect of the condition, including the presence of the stage of development. The correlation may be qualitative, quantitative, or both qualitative and quantitative. Typically a biomarker is a compound, compound fragment or group of compounds. Such compounds may be any compounds found in or produced by an organism, including proteins and peptides, nucleic acids, amino acids, sugars and other compounds. A biomarker can be described as "a characteristic that is objectively measured and evaluated as an indicator of a condition, such as gender, age and viability, or nourishment status". A biomarker is any identifiable and measurable indicator associated with a particular condition or disease where there is a correlation between the presence or level of the biomarker and some aspect of the condition, including the presence of the stage of development. The correlation may be qualitative, quantitative, or both qualitative and quantitative. Biomarkers also may comprise compounds that are metabolites of tracer precursor molecules that had been introduced to the ovulating parent, and are then metabolized by the embryo during its development, excreting tracer metabolites as biomarkers.

A database set of control spectra collected from control samples is preferably initially compiled by choosing samples of a specific gender of a given chicken race. A complete library or database was contemplated as containing samples of both genders.

Specifically, the typing is based on spectral differences that appear throughout portions of both the ultraviolet and visible range. At present the origin of these differences is unknown, but it may be due to intrinsic absorption differences at the molecular level.

Additionally, the calculating means comprises software means resident in a computer.

It may be appreciated by one skilled in the art that additional embodiments may be contemplated, including systems and methods for characterizing other egg components and their constituents, such as, but not limited to, allantoic fluid, egg yolk, egg white, and egg shell.

The present invention also relates to egg selections, and after hatching, to a chick or a chick population obtainable by the process.

The present invention also relates to a method, system and food product for the in ovo gender, viability and/or developmental stage determination of embryos of oviparian species in more general terms, i.e. not limited to fowl, or even more specifically to *Gallus Gallus Domesticus*.

Accordingly, the present invention also relates to a process for the determination of the in ovo gender, viability and/or developmental stage of an embryo of an oviparian species. The present process further relates to the selection of male eggs and female eggs, and to the production of groups of live animals using these selected eggs. Oviparous animals lay eggs, with little or no other embryonic development within the mother. This is the reproductive method of most fish, amphibians, reptiles, all birds, and most insects, mollusks and arachnids. Cultivation of oviparian animals and their eggs caters for an ever growing part of the global protein supply, as well as for various other large scale industrial processes, such as production of vaccines. At present, the most important processes for the cultivation of oviparian animals include the rearing of avian species, such as poultry, and aquaculture, i.e. the farming of aquatic organisms such as fish, crustaceans and mollusks.

The present invention also relates to a method for identifying gender, viability and/or developmental stage of an oviparian embryo in ovo, comprising a. providing a food product comprising a tracer precursor material comprising at least one tracer precursor compound which is acceptable for use as an additive in food to the ovulating parent, and b. incubating an egg for a suitable period to allow for metabolism of the tracer precursor compound to form at least one tracer compound in a suitable amount; and c. subjecting the egg, or a sample from the egg to an analysis to determine the presence and amount of the one or more tracer compounds, and d. determining gender, viability and/or developmental stage of the oviparian embryo from the data obtained in step (c).

Fertilized eggs of most oviparian species tend to deliver an about equal distribution of male and female animals. However, for various reasons, in hatchery management, it may be desirable to separate animals based upon various characteristics, in particular gender. In commercial domestic chicken and egg production for instance, incubation and rearing of male chicks is highly undesirable, leading to the culling of billions of male chicks every year. In shrimp and prawn production, it is desirable to raise an exclusively female population, due to the processes required to induce maturation of eggs.

Currently, in both cases, mixed populations of hatched animals are subjected to sexing by visual assessment of the juvenile animal, of sometimes even the adult population where juveniles do not have suitable traits. In either case, this is a highly time consuming process, requiring highly skilled operators, and is typically very stressful for the animals. Also, where adult animals are sexed, the entire populations needs to be reared to a minimum age, while only half of the thus reared animals are used for proliferation after separation. Further problems may occur where the presence of e.g. a male population may lead to reduced productivity due to e.g. cannibalism and reduced farming density, as reported for instance from the fresh water prawn *M. rosenbergii*.

Also in fish farming, the determination of the gender or sex of a fish would allow to rear predominantly male or female monosex populations, thereby allowing to target growth and health of the population more specifically, as is presently practiced for Nile tilapia, which are cultivated preferably as an all-male population. Again, in most fish, only at a late juvenile or the adult stage, the gender can be determined by visual inspection, so that complicated breeding patterns and specific populations have to be established with "super male" hybrids, which may be prone to enhance the presence of genetic disorders, and which may also be prone to certain illnesses related to the very genetic small population spread.

Furthermore, there is a percentage of eggs that are unfertilized, or do not comprise a viable embryo at the beginning of the incubation period, which greatly reduces the capacity of the incubators employed at hatcheries, in particular for poultry eggs.

As a result, an incubation capacity is required which is at least twice as large as necessary if an early gender selection would be available, permitting the selection of primarily only male or female embryos.

Accordingly, it would be of great value for the environment, by reduction of the amount of energy and other resources required, but equally for the elimination of unnecessary animals by culling, as well as reduction of stress for the newly hatched animals, if an early stage method was available that allowed to determine the gender of avian embryos prior to the incubation phase, also permitting to strongly increase the capacity of hatcheries. A further benefit would be if the method also permitted to select viable embryos over unfertilized and/or otherwise nonviable eggs, increasing the efficiency of the hatching process further.

For fish or shrimp, various largely PCR or antibody based methods have been published. However, these are rather costly and complex.

Hence there remains a need for a faster, and easier to apply method for the non-destructive determination of gender, developmental stage and/or and viability of an oviparian animal embryo in ovo.

It is therefore a further object of the present invention to provide a method for identifying a characteristic of an embryo of an oviparian species in ovo, the method comprising: (a) subjecting a sample of material associated with the egg comprising the embryo to a mass spectrometric analysis and recording retention time index and corresponding mass and mass for each signal detected; (b) correlating the mass corresponding to each signal to a reference database of biomarker masses specific for the species to form a correlation between one or more signals and one or more reference biomarkers; (c) confirming the correlation between each correlating signal and a reference biomarker by matching the mass spectrum of each correlating signal with the mass spectrum of the correlating reference biomarker using a similarity measure, to define at least one positively correlating signal; and (d) measuring the intensity of each positively correlating signal and scoring its absolute or relative signal intensity; and (e) applying a threshold to the score value obtained from the discrimination function to determine the characteristic for the embryo associated with the presence and concentration of the correlated biomarker.

It is a further object to provide such instrumentation for use in hatcheries. It is yet a further object to provide a system capable of performing real time online analysis of eggs at remote locations, such as hatcheries or aquacultures. These and other objects are addressed by the apparatus and process of the present invention. Accordingly, the present invention relates to a method for identifying one or more biomarkers associated with a characteristic of an embryo of an oviparian species in ovo, the method comprising: analyzing a multitude of samples from a multitude of eggs of a species with a known gender in a mass spectrometer to obtain a multitude of mass spectra to establish a biomarker pattern, and performing a pattern recognition on the mass spectra to obtain a biomarker pattern, and determining biomarkers and biomarker levels associate with at least one characteristic of an embryo based on the biomarker pattern.

In a further aspect, the subject process also relates to a multitude of viable female eggs, forming a predominantly male or predominantly female egg selection. In yet a further aspect, the subject process also relates to a juvenile animal population obtainable by the method according to the invention. In yet a further aspect, the subject process also relates to the use of a multitude of eggs obtainable from the process for animal and/or human food production, for the production and/or isolation of cosmetic, medical and/or nutritional compounds, for methane production through fermentation, vaccine production, and/or high quality fertilizer production.

In yet a further aspect, the subject process also relates to an oviparian animal embryo gender detection and analysis system, comprising a preferably fully automated apparatus for the execution of the subject methods.

In yet a further aspect, the present invention relates to a method for identifying gender, viability and/or developmental stage of an oviparian embryo in ovo, comprising (a) providing a food product comprising a tracer precursor material comprising at least one tracer precursor compound which is acceptable for use as an additive in food to the ovulating parent, and (b) incubating an egg for a suitable period to allow for metabolism of the tracer precursor compound to form at least one tracer compound in a suitable amount; and (c) subjecting the egg, or a sample from the egg to an analysis to determine the presence and amount of the tone or more tracer compounds, and (d) determining gender, viability and/or developmental stage of the oviparian embryo from the data obtained in step (c).

In a further aspect, the present invention also relates to a food product for the determination of embryo gender, viability and/or developmental stage, and to the use of a trace precursor compound in animal food.

The present invention also relates to the system, wherein the gender identification facility is implemented in software on an electronic device interfaced with the spectroscopic system; and preferably wherein the identification facility comprises software means resident in a computer.

Figure 1:
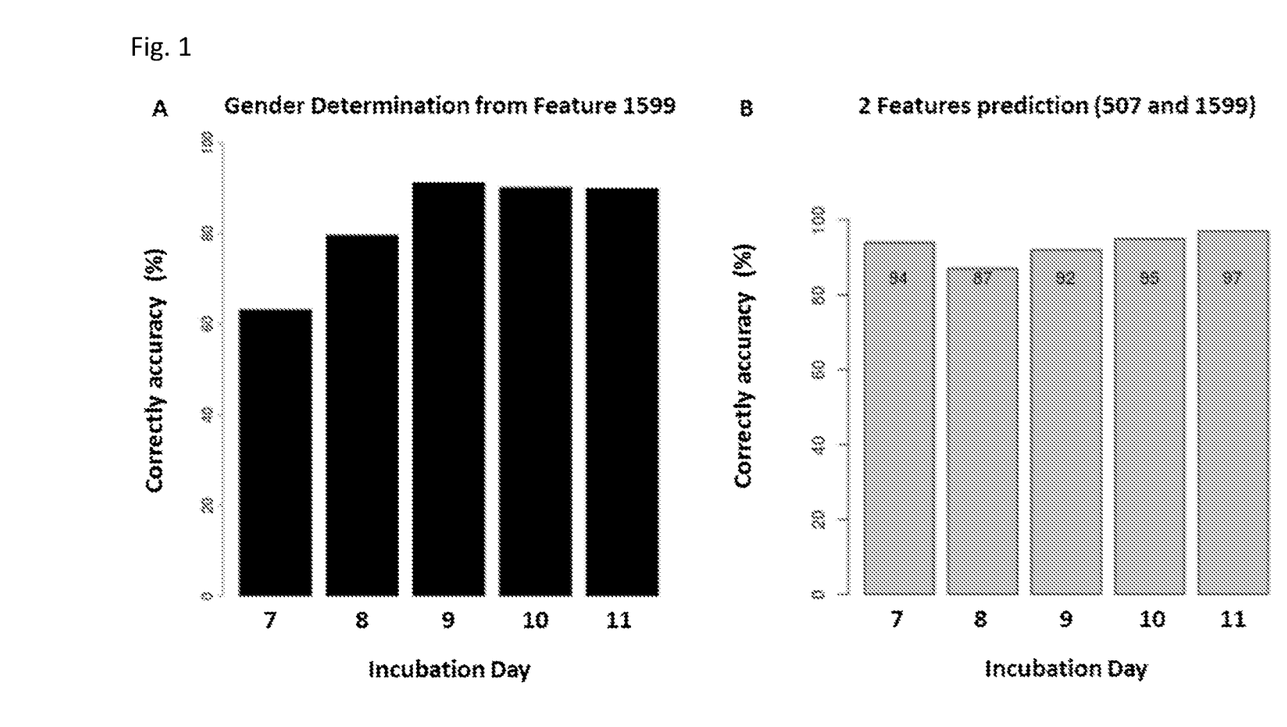
FIG. 1 depicts A) Logistic Regression Classification Model on Single Feature, being the concentration of 3-[(2-aminoethyl)sulfanyl]butanoic acid, with an accuracy of more than 90% for the gender prediction; and B) Logistic Regression on 2 Features: when applying a logistic regression models on two biomarkers, the accuracy could be increased to >95% accuracy from Day 10.
Figure 2:
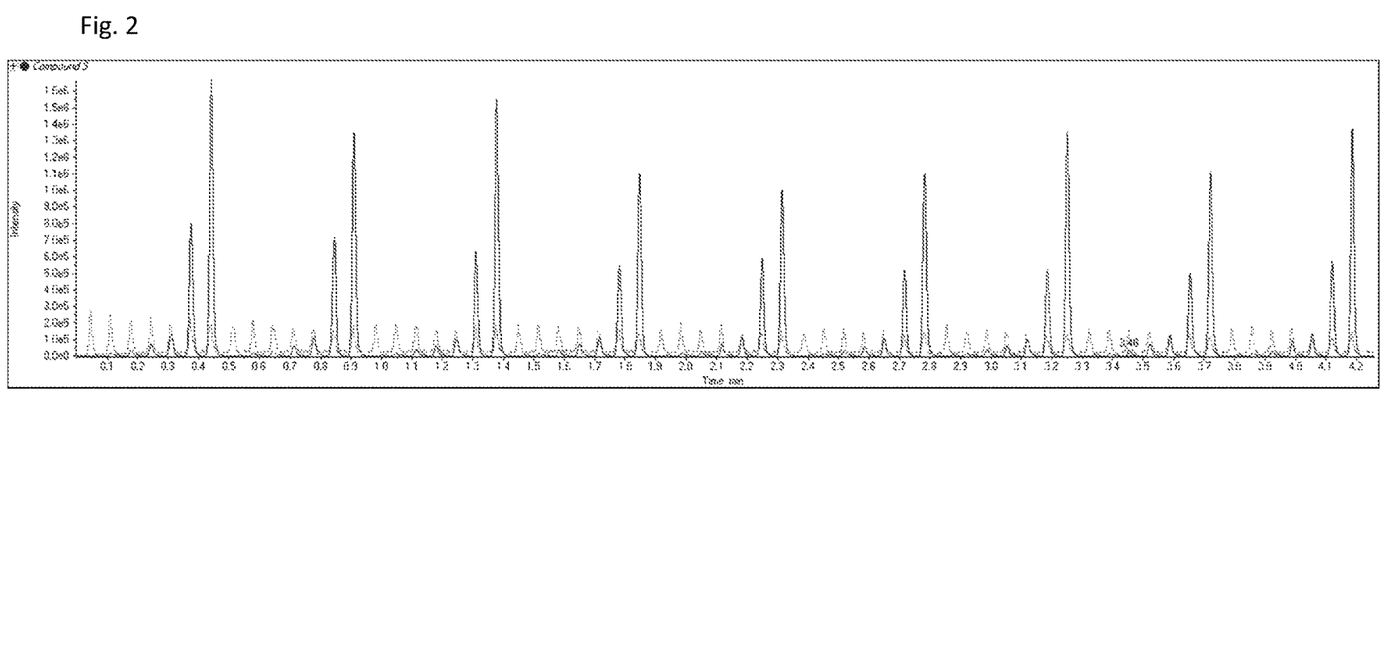
FIG. 2 shows an LDPD spectrum of the biomarker according to the invention in a serial test, automated high throughput test. The method allows not only to measure the presence of the biomarker, but also the absolute concentration, in less than 10 seconds per individual sample.

FIG. 1 depicts a A) Logistic Regression Classification Model on Single Feature. A single predictor models was evaluated for all measured features and the best accuracy was observed using Feature 1599, which provides >90% accuracy from Day 9. B) Logistic Regression on 2 Features. Logistic regression models were evaluated on all possible pairs of measured features. After checking the robustness of the measurements the best performance was achieved by combination of Features 1599 and 507, providing >95% accuracy from Day 10.

The present method thus relates to a relative determination of a property, such as the gender. This may be increased significantly by adding additional features, and by e.g. removal of outliers, or eggs with dubious features, thereby increasing the accuracy significantly.

Figure 3:
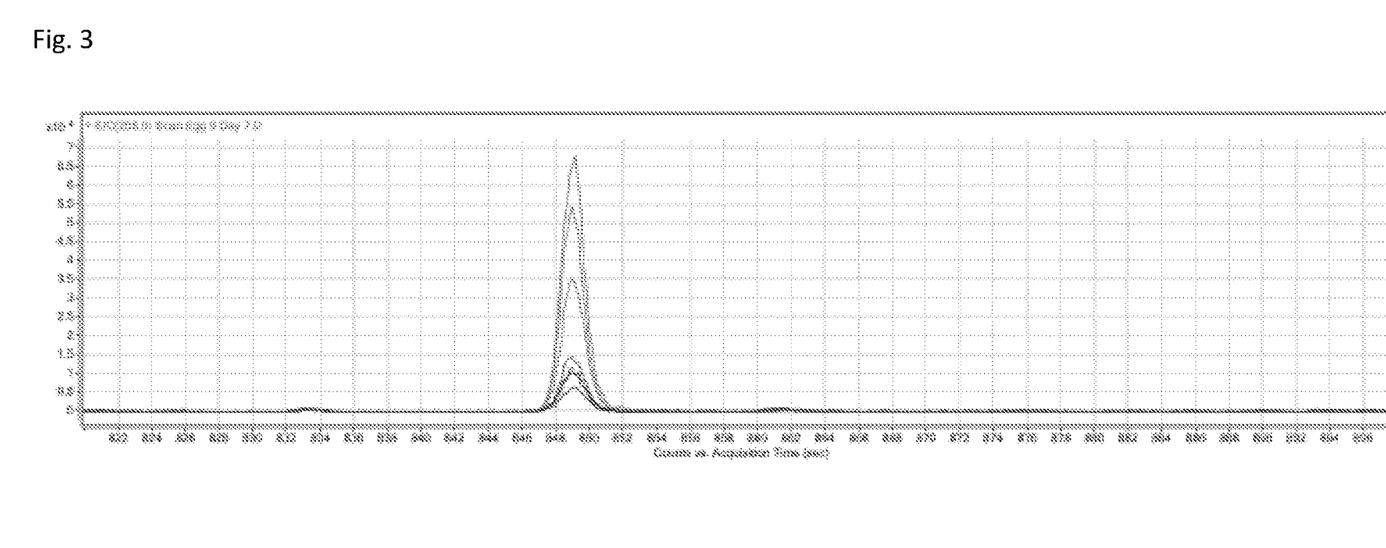
FIG. 3 shows chromatograms of compounds with various mass peaks ranging from 220 to 145, extracted at 850 seconds from male (dark grey color) and female (light grey color) samples.

FIG. 3 shows chromatograms of compounds with various mass peaks ranging from 220 to 145, extracted at 850 seconds from male (dark grey color) and female (light grey color) samples.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. Many oviparian species are reared commercially.

"Aquaculture" involves cultivating freshwater and saltwater populations under controlled conditions, and can be contrasted with commercial fishing, which is the harvesting of wild fishes and other sea animals.

"Fish" species herein includes all gill-bearing aquatic craniate animals that lack limbs with digits. Included in this definition are presently living hagfish, lampreys, and cartilaginous and bony fish species, whether marine or sweat water fishes. Important fish species or families that cultivated commercially include members of the Cyprinidae family of freshwater fishes, such as carps, true minnows, and their relatives, for example, barbs, barbels and Catfishes and Pangasiidae, Grass carp, common carp, Bighead carp, Silver carp, Catla, Crucian Carp, and the likes; Salmonidae including salmon, trout, chars, freshwater whitefishes, and graylings, e.g. Atlantic salmon, Sea trout and Rainbow trout; Serranidae such as the barramundi or Asian seabass, Japanese seabass, European seabass; Latidae; Sparidae, such as sea breams and porgies; Cichlidae such as Nile or Mozambique tilapia, and Acipenseridae, such as Atlantic or beluga sturgeon.

"Crustaceans" herein refers a group of arthropod species that have separate sexes, and reproduce sexually, which includes such familiar animals as crabs, lobsters, crayfish, shrimp.

"Crabs" herein are decapod crustaceans of the order Brachyura.

"Shrimp" and/or "prawn" herein refers to any kind of cultivatable crustacean, such as the salt or brackish water aquacultured Penaeidae, preferably the *Penaeus* genus of prawns, including the giant tiger prawn, *P. monodon*, Pacific white shrimp, *Litopenaeus vannamei*; Western blue shrimp (*P. stylirostris*); Chinese white shrimp (*P. chinensis*; Kuruma shrimp (*P. japonicus*); Indian white shrimp (*P. indicus*); Banana shrimp (*P. merguiensis*); and other members of the Caridea or Dendrobranchiata families; and fresh water aquacultured crustaceans such as for instance for *Macrobrachium rosenbergii. M. nipponense* and *M. malcolmsonii*; crayfish from the genera Astacoidea and Parastacoidea, such as *Procambarus clarkii*; and cultivable lobster species from the Nephropidae and Homaridae families, as well as spiny lobsters from the family of Palinuridae.

"Mollusks" herein refers to a large phylum of invertebrate animals known as the Mollusca order, including cephalopod mollusks, such as squid, cuttlefish and octopus; bivalve shells such as polyplacophora, scaphopods and tusk shells which have separate sexes, and wherein fertilization is external.

The terms "avian" and "bird" as used herein, include males or females of any avian species, but are primarily intended to encompass poultry which are commercially raised for eggs or meat. Accordingly, the terms "bird" and "avian" are particularly intended to encompass chicken, turkeys, ducks, geese, quail, doves, ostrich, emu, and pheasants.

The term "incubation" herein refers to the process by which oviparian animals, such as birds hatch their eggs, and to the development of the embryo within the egg after leaving the adults' tract. The incubation period herein refers to the uninterrupted time during which a particular egg is subjected to conditions emulating the brooding until the hatching, i.e. emergence of the hatchlings, including any handling or transfers from e.g. an incubator to a hatchery unit, provided the development of an animal is not stalled.

The term "in ovo" as used herein, refers to embryos contained within an egg prior to hatch. The present invention may be practiced with any type of bird, fish, mollusk, reptilian or crustacean egg, including, but not limited to, (domesticated) chicken, turkey, duck, goose, quail, and pheasant eggs, fish, such as carp, salmonid or tilapia eggs; shrimp or prawn eggs, and mollusk eggs.

The terms "injection" and "injecting" herein encompass methods of inserting a device (typically an elongate device) into an egg or embryo, including methods of delivering or discharging a substance into an egg or embryo, methods of removing a substance (i.e., a sample) from an egg or embryo, and/or methods of inserting a detector device into an egg or embryo.

The term "mass spectrometry" herein refers an analytical technique that sorts ions based on their mass. Mass spectrometry typically is used for chemical analysis in many situations and might be applied to any sample from a complex mixture of petroleum to the products of genetic engineering. In simple terms, a mass spectrum will give a picture of the exact chemical composition of a sample.

A mass spectrum is a plot of the ion signal as a function of the mass-to-charge ratio. These spectra are used to determine the elemental or isotopic signature of a sample, the masses of particles and of molecules, and to elucidate the chemical structures of molecules. Mass spectrometry ionizes chemical compounds to generate charged molecules or molecule fragments and measures their mass-to-charge ratios.

In a typical MS procedure, a sample, which may be solid, liquid, or gas, is ionized, for example by bombarding it with electrons. This may cause some of the molecules to break into charged fragments. These ions are then separated according to their mass-to-charge ratio, typically by accelerating them and subjecting them to an electric or magnetic field. Ions of the same mass-to-charge ratio will undergo the same amount of deflection.

The ions are detected by a suitable mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses or through a characteristic fragmentation pattern. In the present context, mass spectrometry is applied to identify, and to detect suitable biomarkers. Mass spectrometry (MS) is a valuable analytical technique because it measures an intrinsic property of a molecule, its mass, with very high sensitivity. MS can therefore be used to measure a wide range of biomarker molecules and a wide range of sampled materials. Correct sample preparation is known to be crucial for the MS signal generation and spectra resolution and sensitivity. Sample preparation is therefore a crucial area for overall feasibility and sensitivity of the analysis.

Preferred methods for the mass spectrometric characterization of biomarkers include matrix-assisted laser desorption ionization (MALDI) and electrospray ionization (ESI). Either may advantageously be can be combined with time-of-flight (TOF) or other types of mass spectrometric sensors to determine the mass and/or fragmentation pattern of a biomarker. Preferably, mass spectrometry may be employed in tandem with chromatographic and other separation techniques herein.

MALDI operates by pulsing a sample with lasers. This treatment vaporizes and ionizes the sample. The molecular weights (masses) of the charged ions are then determined in a TOF analyzer. In this device, an electric field accelerates the charged molecules toward a detector, and the differences in the length of time it takes ionized fragments to reach the detector, i.e. their time-of-flight, to reveal the molecular weights of the biomarkers, whereby smaller compounds reach the detector earlier.

This method generates mass profiles of the sample—that is, profiles of the molecular weights and amounts of compounds in the mixture. These profiles can then be used to identify known biomarkers from biomarker databases.

With an ESI-MS interface to liquid chromatography (LC/MS/MS), the eluting compounds from the LC-column are introduced into the ion source of the mass spectrometer. A voltage is applied to a fine needle. The needle then sprays droplets into a mass spectrometric analyzer where the droplets evaporate and biomarker ions are released corresponding to a variety of charge states that are fragmented and from where the composition can be determined. Alternatively, SPE (solid phase extraction), or gas chromatography can be coupled with the Mass spectrometer. In particular SPE/MS/MS was found useful for automated and high throughput industrial application of the present method, such as using an Agilent Rapidfire MS apparatus (Rapidfire is a registered trade mark of Agilent Inc.); or a laser diode or thermal ion desorption LDID apparatus.

Tandem mass spectrometry (MS/MS) involves activation of a precursor ion via collisions with a target gas and may produce charged and neutral fragments. The nature of the fragment ions, as well as their intensities, is often indicative of the structure of the precursor ion and thus can yield useful information for the identification of unknown analytes, as well as providing a useful screening technique for different classes of analytes. Activation via multiple collisions both prolongs the activation time and enables higher energies to be deposited into precursor ions. Higher collision gas pressures also imply higher collision relaxation rates.

Preferably the determination of the embryo characteristic according to the present invention is performed as a non-destructive method, i.e. allowing the thus tested embryos to grow, if so desired, or to subject it to further steps such as in ovo vaccine production, provided the embryo is viable.

The term "allantoic fluid" herein encompasses allantoic fluid with or without the presence of other egg materials as derived from avian eggs. For example, the term allantoic fluid may include a mixture of blood and allantoic fluid. Embodiments of the present invention are not limited to extracting material from the allantoic fluid or from areas near the upper surface of an egg. Removal of material from the allantoic fluid as described herein is provided as merely one example of possible embodiments of the present invention. Various materials including but not limited to amnion, yolk, shell, albumen, tissue, membrane and/or blood, may be extracted from an egg and assayed to submit to a spectrophotometric analysis, to identify the gender of the embryo, as described below.

Where desired, material may be extracted from eggs having virtually any orientation. The term "predetermined location" herein indicates a fixed position or depth within an egg. For example, a device may be injected into an egg to a fixed depth and/or fixed position in the egg. In alternative embodiments, the injection may be carried out based on information obtained from the egg, e.g. regarding the position of the embryo or the subgerminal cavity within the egg.

Alternatively, in particular in the case of mollusk, fish or shrimp eggs, the high translucency of such eggs as well as their comparatively small size when compared to avian eggs may allow for a direct, non-invasive analysis through direct, non-invasive measurements on entire eggs.

The term "comparing the spectra" advantageously may include a univariate or preferably multivariate analysis of the measured spectra, and a determination of the association of an avian embryo with a certain population. The step may comprise determining the presence of certain signal peaks in the spectrum by multivariate statistical analysis of the spectral data. The multivariate statistical analysis program preferably comprises a principal components analysis program, and/or a partial least-squares regression analysis program. The subject invention thus also pertains to a process, apparatus and system for determination of gender and/or viability of an avian embryo in ovo, comprising multivariate statistical analysis program, as well as a microprocessor implemented process for the determination thereof.

Accordingly, the comparison preferably comprises an estimation of the likelihood of a gender for a sample using multivariate analysis of the measured spectra, and a determination of the association of an avian embryo with a certain population. Advantageously, this is performed using Partial Least Squares Discriminate Analysis (PLS-DA).

The process preferably includes the mathematical treatment of the tracer compound data and includes a multivariate analysis such as PCA (Principle Component Analysis), preferably followed by a supervised analysis, more preferably PLS-DA (Partial Least Squares-Discriminate Analysis) or even more preferably Orthogonal PLSDA, or similar suitable statistical approaches.

The pattern matching step within the subject process will identify a certain similarity measure. Using the similarity measure, the correct structure of the biomarker is confirmed. This confirmation is made by spectral matching. The spectral matching is performed by comparison of the sample spectra and the reference spectra in the database. For a positive identity at this stage suitable correlation is required in order to confirm the accurate determination. Suitable threshold values and similarity measures will be apparent to those skilled in the art.

This process attempts to reduce large amounts of data to a manageable size and apply a statistically driven model in order to determine latent variables indicative of hidden relationships between the observed data.

The Gender Identification facility then filters the sample data, which will identify clusters of interest among the samples. The clusters represent similarities among the samples and are used to identify the gender profiles. Preferably the analysis includes Principal Component Analysis (PCA) and PLS-DA.

PCA employs mathematical algorithms to determine the differences and similarities in a data set. PCA transforms a number of possibly related variables into a smaller number of unrelated variables which are referred to as principle components. The first principle component accounts for as much of the variability in the data as possible. Each additional component attempts to account for as much of the remaining variability in the data as possible. The collected data may be arranged in a matrix and PCA solves for "eigenvalues" and "eigenvectors" of a square symmetric matrix with sums of squares and cross products.

The eigenvector associated with the largest eigenvalue has the same direction as the first principle component. The eigenvector associated with the second greatest eigenvalue determines the direction of the second principle component. The sum of the eigenvalues equals the trace of the square matrix and the maximum number of eigenvectors equals the numbers of rows (or columns) of this matrix. Once determined, it is possible to draw screen plots of the calculated eigenvalues. Those skilled in the art will recognize that a number of different algorithms may be used to calculate the eigenvalues and eigenvectors. The data is displayed using two plots: i) the scores plot which shows the group clustering and ii) the loadings plot in which the spectral data responsible for the group clustering are identified as those being the greatest distance from the origin.

The process according to the present invention preferably comprises (a1) providing a sample comprising an egg fluid; and (a2) acquiring the spectrum from the sample. Preferably, step (b) further comprises the step of normalizing intensity effects due to a concentration difference between any two samples. Optional step (a3) removes preferably turbidity from the samples, by a suitable method such as ultrafiltration or centrifugation.

Preferably, the embryo is an avian embryo, a reptilian embryo, a crustacean, a fish, or a mollusk. Most preferably, avian embryos are subjected to the test due to the high importance of the poultry cultivation, and due to the comparatively large i.e. of the eggs that allows sampling.

The present method advantageously may determine whether an embryo in an egg is viable and male, or viable and female, and to separate the tested eggs into a multitude of viable male eggs from a multitude of viable female eggs, and a multitude of non-viable eggs, to form a predominantly male or predominantly female egg, or predominantly non-viable egg selection. If so desired, the viable female or male egg selections may be subjected to incubation and the hatching process, to form a predominantly female or male animal population.

The features that characterize the invention, both as to organization and method of operation, together with further objects and advantages thereof, will be better understood from the following description used in conjunction with the accompanying drawing. It is to be expressly understood that the drawings are for the purpose of illustration and description and is not intended as a definition of the limits of the invention. These and other objects attained, and advantages offered, by the present invention will become more fully apparent as the description that now follows is read in conjunction with the accompanying drawing.

Methods and apparatus according to embodiments of the present invention may be utilized for identifying one or more characteristics of an egg at any time during the embryonic development period, also referred to as the incubation period thereof. Embodiments of the present invention are not limited to a particular day during the embryonic development period.

The method of the invention may be implemented in two ways; using internal standards to provide a reference for quantitating signal intensity, and without such standards. Thus, in one embodiment, one or more internal standards are added to the sample prior to analysis by mass spectrometry. Preferably, the internal standards are labelled. Advantageously, the absolute signal intensity for each biomarker signal may then be scored by measuring the biomarker signal intensity and comparing it to the signal intensity of one or more known internal standards. In the alternative implementation, the sample is processed without the addition of internal standards. In such an embodiment, the relative signal intensity is scored by measuring the ratio between the individual biomarker signal intensities in a sample and the reference signal intensity for a sample group.

The similarity measure preferably involves correlating retention index and fragmentation pattern associated with a positively correlated signal.

Further, statistically significant similarities may be detected and registered as relevant biomarker identities, or multiple biomarker identities. Determining statistically significant similarities involves using data bases as well as algorithms developed to meet the demands of the methodology.

This may include, in particular when determining the usefulness of a biomarker for a new species applying a supervised multivariate analysis, preferably Partial Least Squares Discriminate Analysis, PLS-DA or Orthogonal Partial Least Squares Discriminate Analysis to the data.

Preferably, the characteristic that is to be determined comprises gender, age, developmental stage and/or viability of the embryo in the egg. For industrial application, a multitude of eggs are examined for one or more embryonic characteristics.

In the method according to the invention, a database may be established for a certain species by screening the biomarkers present in a sample and eliminating undesired signals on the basis of the retention time index, which correlates with the time of arrival of the compound at the mass detector. Hence many sequences can ben can be analyzed in minutes and given biomarkers identified with high confidence. The method is hence automatable, high-throughput and operable by relatively unskilled technicians, and therefore suitable for use at remote locations, e.g. hatcheries and chicken or fish farms.

The sample can be subjected to mass analysis without prior separation procedures. In such an embodiment, the sample is preferably analyzed by direct infusion using e.g. static nano-electrospray principles, flow injection analysis or flow injection with sample enrichment.

The mass spectrometer system is preferably electrospray ionisation (ESI) MS, matrix-assisted laser desorption ionisation-time of flight (MALDI-TOF) MS or surface enhanced laser desorption ionisation-time of flight (SELDI-TOF) MS, or Laser Diode Ionisation Desorption (LDID) MS.

In particular SPE/MS/MS was found useful for automated and high throughput industrial application of the present method, such as using an Agilent Rapidfire MS apparatus (Rapidfire is a registered trade mark of Agilent Inc.); a Phytronics The LDTD (Laser Diode Thermal Desorption) Ion Source (LDTD is a registered trade mark of Phytronics Inc.).

As set out above, the present invention also relates to a food product for the determination of embryo gender, viability and/or developmental stage, and to the use of a trace precursor compound in animal food. Applicants surprisingly found that adding suitable precursor compounds in food of the ovulating parent lead to a different expression of metabolites of the precursor compounds in the egg during the embryonic development.

As a result, the eggs show a measureable variation of certain metabolites, depending on a characteristic of the embryo, such as the gender of the embryo. Preferably, the at least one tracer precursor compound is selected from a compound which is listed as a permissible food additive by the US Food and Drug Administration (FDA) and/or the European Commission. Particularly suitable tracer precursor compound may be selected from Butylated hydroxyanisole (BHA) and/or the related compound butylated hydroxytoluene (BHT), which are phenolic compounds suitably added to foods to preserve fats. BHA herein refers to a mixture of the isomers 3-tert-butyl-4-hydroxyanisole and 2-tert-butyl-4-hydroxyanisole; while BHT refers to 3,5-di-tert-butyl-4-hydroxytoluene; also known as methyl-di-tert-butylphenol; 2,6-di-tert-butyl-para-cresol. BHA and BHT are known antioxidants; it is believed that oxygen reacts preferentially with BHA or BHT rather than oxidizing fats or oils, thereby protecting them from spoilage. In addition to being oxidizable, BHA and BHT are fat-soluble. The tracer precursor material is preferably added to the food product in an amount calculated to provide a predetermined concentration of the, or each tracer compound in the product. Preferably, the tracer precursor material is added to the product in an amount calculated to provide a concentration of the or each tracer compound in the egg or egg sample at a concentration in the range from 5 ppb-5 ppm, more preferably in the range from about 10-1000 ppb, and yet more preferably 50-500 ppb.

The tracer material may advantageously comprise more than one tracer compound, the relative amounts of the tracer compounds being selected to provide an identifiable characteristic for the gender, viability and/or developmental stage of an oviparian embryo, wherein the analysis of the egg or egg sample is performed in order to identify the characteristic relative amounts of the tracer compounds. The analysis is preferably performed using a mass spectrometer, such as for instance an ion mobility sensor. The sample may be first subjected to liquid chromatography, gas chromatography or a combination of gas chromatography, which is preferably coupled with a suitable sensor. An alternative to the MS sensor may be a flame photometric detector.

Preferably, the at least one of the tracer compounds present in a sample taken from the egg may be separated, derivatised or concentrated prior to analysis, after the step of analyzing an egg fluid invasively or non-invasively. Preferably, the embryo the characteristic of which is to be investigated is an avian embryo, a reptilian embryo, a crustacean embryo, a fish embryo or a mollusk embryo. More preferably, the embryo is an avian embryo, preferably of the species *Gallus gallus domesticus*, or wherein the embryo is an embryo of a crustacean species selected from the group comprising Peneidae, Astacoidea and Parastacoidea, Macrobrachiae; Astacoidea; Parastacoidea; Nephropidae and Homaridae, or wherein the embryo is an embryo of a fish species, preferably selected from carp, tilapia, catfish, sea bream, sea bass, tuna, mackerel, bonitos, or yellowtail.

The present invention also relates to a food product for use with ovulating parent animals, comprising a suitable amount of a tracer precursor compound.

The estimation of the likelihood of a gender for a sample preferably comprises applying a supervised multivariate analysis, preferably Partial Least Squares Discriminate Analysis, PLS-DA or Orthogonal Partial Least Squares Discriminate Analysis to the data.

Advantageously, outliers may be are removed from the population, thereby increasing the certainty for the determination even more, while also contributing to the stream of eggs to be used for other purposes.

The present method further advantageously comprises separating the eggs into multitudes of male or female eggs; it may also further advantageously comprise determining the viability of the embryo, and separating eggs into one or more, preferably multitudes, of viable eggs and non-viable eggs.

The present method, wherein outliers are removed from the population, further advantageously comprises determining whether an embryo in an egg is viable and male, or viable and female, and separating a multitude of viable male eggs from a multitude of viable female eggs, and outliers, to form a predominantly male or predominantly female egg selection.

The present method further advantageously comprises subjecting the viable female or male egg selections to an incubation and hatching process to form a predominantly female or male animal population.

Viability of an embryo may advantageously be determined using the measured biomarkers. Fr non-fertilized eggs, as well as deceased embryos after a certain period of time (i.e. minutes after end of metabolism, the measured results are clearly entirely outside the measurement window, leading to outliers that are removed from the viable eggs. Equally, at least in the case of avian embryos, when samples of e.g. the allantois are used, these very quickly after the end of the metabolic activity will become perturbed and eventually yellow due to the dissolution of the membranes that keep the egg yolk separated. Additionally, the heartbeat or flow of blood can be measured, to determine embryonic metabolic activities.

The present invention also relates to the use of a multitude of eggs obtainable from the method disclosed herein for animal and/or human food production, for the production and/or isolation of cosmetic, medical and/or nutritional compounds, for methane production through fermentation, for vaccine production, and/or high quality fertilizer production.

The following, non-limiting examples are provided to illustrate the invention.

Example 1

Sample Shipment and Storage

For biomarker discovery, multiple analytical metabolite profiling platforms were employed, these were the biogenic amines, negative polar lipids, untargeted global profiling, and GC-MS.

In the discovery phase 100 samples were analyzed. Another set of 350 samples, from eggs with different backgrounds in nutrition and race, were analyzed for the confirmation phase, finding biomarkers for gender and age were found in at least two platforms.

The first 150 samples of allantoic fluid (from brown chicken) were collected on incubation day 7-11, and stored at −80° C.

The genetic gender determination data for these samples was prepared using a PCR method. Samples per gender per day were selected, while excess samples of the current set were used for NMR analysis. The metabolic profile of these samples was then analyzed using the amine, polar negative lipids, CG-MS (for sugar compounds) and global profiling platforms.

Another 300 allantoic fluid samples were collected at the hatchery for incubation days 7-11 brown chicken.

Genetic gender analysis was provided, but not used until statistical model building. These samples were used to confirm features found previous global profiling analysis. In addition, 59 samples collected from white eggs (Hey line CV 24) and also used for this confirmation study.

Aliquots

Samples were thawed overnight at 4° C. before aliquotting. Samples were vortexed and manually aliquoted as follows: 5 µL for amine profiling, 50 µL for polar negative lipid profiling and 100 µL for GC-MS (sugar compound analysis). The quality control (QC) pool was generated by taking equal amounts from each sample followed by thorough mixing.

Batch Design

For the discovery phase, samples were randomized and distributed over two batches for the amines measurements. For negative lipids and global profiling, the samples were run in one batch. Replicates were chosen every seven samples and also included were calibration lines, QCs and blanks. QCs were analyzed every 10 samples, they are used to assess data quality and to correct for instrument response. Blanks are used to subtract background levels from study samples.

The raw data were pre-processed using Agilent MassHunter Quantitative Analysis software (Agilent, Version B.05.01).

Amine Profiling

All mentioned equipment, supplies and software are from Waters (Etten-Leur, The Netherlands), unless indicated otherwise. The amine platform covers amino acids and biogenic amines employing an AccQ-tag derivatization strategy adapted from Waters. Briefly, allantoic fluid samples (5 µL each) were spiked with an internal standard solution (Table 1) and followed by MeOH (Actu-All Chemicals) deproteination. The supernatant (10.000 rpm, 10° C., 10 min) was dried under vacuum conditions. The residue was reconstituted in borate buffer (pH 8.5) with 6-aminoquinolyl-N-hydroxysuccinimidyl carbamate (AQC) reagent. The derivatization reaction was neutralized with 10 µl 20% formic acid (Acros Organics). The supernatant (10.000 rpm, 10° C., 10 min) was transferred to vials and placed in a cooled (10° C.) autosampler tray until the injection (1 µL) into the UPLC-MS/MS system.

Data Analysis

Acquired data were evaluated and assigned MRM peaks were integrated using TargetLynx software. MRM peaks were normalized using appropriate internal standards, for analysis of amino acids their 13C15N-labeled analogs were used and for other amines the closest-eluting internal standard was employed. Blank samples were used to correct for background. In-house developed algorithms were applied using the pooled QC samples to correct for shifts in the sensitivity of the mass spectrometer over the batch.

An explorative data analysis was carried out to investigate whether a gender specific feature could be discovered. For this univariate and multivariate standard data analysis methods were applied within BMFL which we usually use to discover biomarkers.

The Samples are then subjected to testing in automated high throughput coupled SPE/M S/MS Rapidfire apparatus, as well as an LDPD Phytronix apparatus. The results indicate that the gender of the viable eggs is determined with higher than 95% accuracy, in less than 10 seconds per sample. FIG. 1 shows the resulting certainty for gender determination, which amounted to more than 95% on day 9 or 10 when two biomarkers were considered together.

Hatching

A series of 25 eggs considered as male or female that had been subjected to sampling a set out above, testing was allowed to proceed to hatching, using a commercial incubation apparatus, and typical incubation conditions. All hatchlings effectively emerged from the eggs, showing the viability of sampling. The hatched chicklets were an either entirely male or female population.

Example 2: Non-Invasive Determination Using Volatiles and Solid Phase Microextraction (SPME)

Volatile sample collection was performed by transferring a single egg to a glass jar sealed with aluminum foil and metal cap. Then, the jar was placed on a heating plate while keeping the temperature inside the jar at 37° C. The egg in the jar was left for 15 minutes to reach equilibrium with the headspace in the jar. A collection fiber material was conditioned before using according to the manufacturer's instructions. Then, the fiber was inserted and the extraction was performed during 50 min. After extraction, the fiber was introduced on the gas chromatograph injector during 5 minutes for desorption of the analytes at 250° C. in splitless mode. The egg was returned to the incubator immediately following the volatile collection. Blanks were made by doing the SPME to an empty jar and before the analysis the fiber reconditioning was carried out to guarantee the absence of peaks and the good quality of the SPME procedure.

The volatiles released from the egg were then measured by gas chromatography on an Agilent Technologies (Wilmington, Del., USA) 7890A equipped with an Agilent Technologies mass selective detector (MSD 5975C). Chromatographic separations were performed on a HP-5MS UI (5% Phenyl Methyl Silox), 30 m×0.25 m ID column with a film thickness of 25 m (Agilent) using helium as the carrier gas at a flow rate of 1 mL/min. A single-quadrupole mass spectrometer with electron ionization (EI, 70 eV) was used. The mass spectrometer was operated in SCAN mode. For the extraction of the volatile compounds a 60 µm PDMS/DVB Stableflex 24 gauge solid phase microextraction (SPME) fiber with holder was used. The raw data were converted into CDF format using MSD Chemstation F.01.00.1903. XCMS script was designed and applied on R software (R version 3.2.0) in order to perform the peak picking. The method used for it was "matchedFilter, with fwhm=4 (Peakwidth), step=0.5 (Mass window) and snthresh=5 (S/N). Metaboanalyst 3.0 was used for statistical analysis. Finally, MassHunter Qualitative Analysis B.005.00 was used to manually verify the most important features according to the results obtained. NIST Mass Spectral Library Version 2.0 was used to identification.

In this process, 1486 features of different masses at the different retention times in seconds were obtained from the TIC of each sample. After the extraction of these features, they were processed by applying a univariate method with a Test using metaboanalyst 3.0 to identify the gender distinguishing features with a confidence of 99%.

Applicants found that a particularly relevant biomarker showing a significantly difference between male and female eggs is butylated hydroxytoluene, which is the derivative of BHT as precursor.

Female eggs exhibited a significantly higher concentration of butylated hydroxytoluene as compared to male eggs. Accordingly, the use of a tracer precursor led to a biomarker that allowed to distinguish between male and female chicken embryos in ovo with high certainty in an entirely non-invasive manner.

The invention claimed is:

1. A method for non-destructively identifying a characteristic of an *Gallus Gallus domesticus* embryo in ovo, the method comprising the steps of:
   (a) obtaining a sample of material associated with an egg comprising the embryo, and
   (b) measuring, by mass spectrometric analysis, a score value for the presence of, and concentration of at least a first biomarker in the sample indicative of the characteristic of the embryo, wherein the at least a first biomarker comprises 3-[(2-amino-ethyl)-sulfanyl]-butanoic acid and wherein the sample comprises allantoic fluid of the embryo, and
   (c) applying a threshold to the score value and concentration obtained in (b) to identify the characteristic for the embryo associated with the presence and concentration of the biomarker, wherein an at least first biomarker comprises an amino compound having a molecular weight in the range of from 140 to 190 g/mole; wherein step (c) further comprises:
      (i) correlating each relevant biomarker signal with a reference biomarker by matching the spectrum of each correlating signal with the expected spectrum of the correlating reference biomarker using a similarity measure, to define at least one positively correlating signal;
      (ii) measuring the intensity of each positively correlating signal and scoring its absolute and/or relative signal intensity; and
      (iii) applying a threshold to the score value obtained from a similarity function to determine the correlated embryo characteristic.

2. The method according to claim 1, wherein the presence and concentration of the biomarker correlates to an embryo being likely to develop into a male adult, or into female adult.

3. A method according to claim 1, wherein a concentration of 3-[(2-amino-ethyl)-sulfanyl]-butanoic acid in an amount of 50 ng/ml or more in the allantoic fluid on day 7, 8 or 9 correlates to a female embryo, while a presence of the biomarker present in less than 50 ng/ml correlates to a male embryo.

4. The method according to claim 1, wherein at least a first and a second biomarker are detected and analyzed, and wherein the absolute and relative amounts of the at least first and second markers are employed to determine the one or more characteristics.

5. The method according to claim 1, wherein a selected characteristic is the likely viability or non-viability of an embryo to achieve full growth to hatching.

6. The method according to claim 1, wherein a selected characteristic is a prognosis for the likely developmental stage and time required for the embryo to progress to hatching under incubation conditions.

7. The method according to claim 1, wherein the mass spectrometric analysis comprises electrospray ionization (ESI) mass spectroscopy, matrix-assisted laser desorption ionization-time of flight (MALDI-TOF) mass spectroscopy or surface enhanced laser desorption ionization-time of flight (SELDI-TOF) mass spectroscopy, SPE/MS/MS, LDTD (Laser Diode Thermal Desorption) Ion Source, and/or use of an Ion Mobility Sensor (IMS).

8. The method according to claim 1, wherein the test sample is processed prior to analysis, and the sample processing comprises sample separation by solid phase extraction (SPE), gas chromatography, single- or multi-phase high-pressure liquid chromatography (HPLC).

9. The method according to claim 8, wherein one or more internal standards of reference biomarkers are added to the sample prior to analysis by mass spectrometry.

10. The method according to claim 1, wherein the absolute signal intensity is scored by measuring the biomarker signal intensity and comparing it to the signal intensity of one or more known internal standards.

11. The method according to claim 1, wherein a multitude of eggs are examined for one or more embryonic characteristics.

12. The method according to claim 1, wherein the method is fully automated.

13. The method according to claim 1, further comprising determining whether an embryo in an egg is viable and male, or viable and female, or non-viable, and separating a multitude of viable male eggs from a multitude of viable female eggs, and one or more non-viable eggs.

14. The method according to claim 13, further comprising sorting viable eggs according to the perceived time until the embryo is likely to hatch.

15. A process for the selective incubation of hatchlings of a oviparian species with a specific characteristic, comprising
   a. providing a multitude of eggs from the species, and
   b. subjecting the eggs to the method according to claim 1 to determine a characteristic of the embryo, and
   c. selecting the eggs with the desired characteristic to form a selected multitude of eggs, and
   d. incubating the selected eggs until one or more of the hatchlings hatch.

* * * * *